United States Patent [19]

Miller

[11] 4,239,888
[45] Dec. 16, 1980

[54] 1-PHENYLURACILS

[75] Inventor: Max W. Miller, Stonington, Conn.

[73] Assignee: Pfizer Inc., New York, N.Y.

[21] Appl. No.: 520,407

[22] Filed: Nov. 4, 1974

[51] Int. Cl.$^2$ .............................................. C07D 239/54
[52] U.S. Cl. .................................. 544/309; 424/251;
544/314
[58] Field of Search ................. 260/260; 544/309, 314

[56] References Cited
U.S. PATENT DOCUMENTS 3,235,358  2/1966  Soboczenski ........................ 260/260

*Primary Examiner*—Paul M. Coughlan, Jr.
*Attorney, Agent, or Firm*—Connolly and Hutz

[57] ABSTRACT

Compounds of the formula

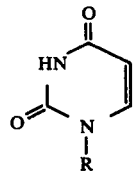

wherein R is

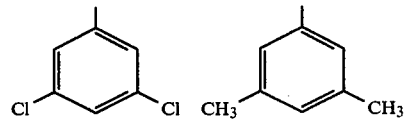

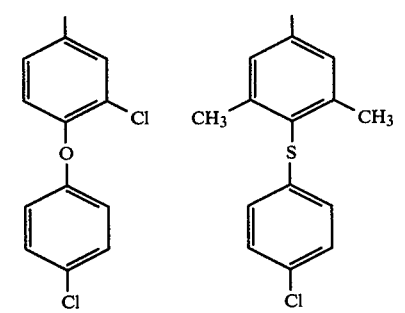

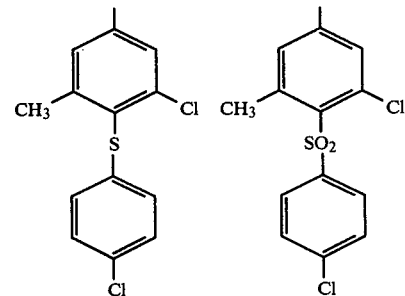

and their utility as coccidiostats.

2 Claims, No Drawings

1-PHENYLURACILS

BACKGROUND OF THE INVENTION

Coccidiosis, a poultry disease, is caused by several species of protozoan parasites of the genus Eimeria such as *I. necatrix, E. acervuliana, E. maxima, E. hagani, E. tenella*. *E. tenella* is the causative agent of a severe and often fatal infection of the ceca of chickens which is manifested by extensive hemorrhage, accummulation of blood in the ceca and the passage of blood in the droppings. Essentially, coccidiosis is an intestinal disease which is disseminated by birds picking up the infectious organism in droppings on contaminated litter or ground. By damaging the intestinal wall, the host animal is unable to utilize its food, goes off its feed, and in untreated cases the disease terminates in either the death of the animal or the survival of unthrifty birds known commonly as "culls".

Much work has been done in this area in developing compounds having anticoccidial activity. For instance, there are effective compounds such as sulfur, sulfa drugs, arsenicals, dihydro-1,3-5-triazines (U.S. Pat. No. 2,823,161); 3-amino-as-triazine complexes with substituted ureas (U.S. Pat. No. 2,731,385); 1-phenyl-3-(3-as-triazinyl) ureas (U.S. Pat. No. 2,762,743); 5-fluorouracil (U.S. Pat. No. 3,017,322); and as-triazine-3,5-(2H,4H) dione (U.S. Pat. No. 2,956,924). Another effective group of compounds for controlling and treating coccidiosis is the substituted bis-thiosemicarbazones of cyclic 1,2-diketones and metal chelates which are the subject of U.S. Pat. Nos. 3,382,266 and 3,622,674. Also found to be effective are the 6-azauracils as disclosed and claimed in my pending CIP patent applications Ser. Nos. 364,672 filed May 29, 1973 (U.S. Pat. No. 3,905,971) and 381,062 filed July 20, 1973 (U.S. Pat. No. 3,912,723).

SUMMARY OF THE INVENTION

Uracil itself is a well-known basic nucleic acid component and as the nucleoside, nucleotide or bound in high molecular weight nucleic acids in all living organisms is devoid of chemotherapeutic import. By correct design of the substituted phenyl sidechains and by attachment of the chain at the correct atom (1-position) of the 6-membered uracil heterocycle, it has now been found that a considerable degree of coccidiostat efficacy is achieved by the so-substituted uracil. This contrasts to the 6-azauracils of my above noted patent applications wherein the parent heterocycle, 6-azuracil itself has a considerable degree of coccidiostat efficacy and the sidechains merely itensified the activity.

The 1-phenyluracil coccidiostat compounds of the present invention are represented by the formula:

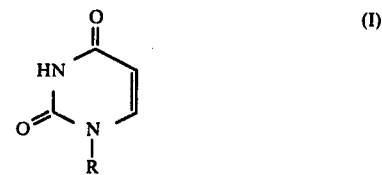

wherein R is:

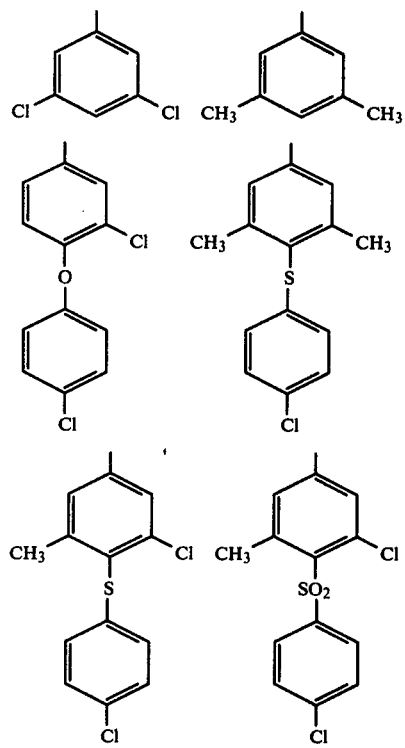

The 1-phenyluracils of the present invention may be prepared by the following reaction sequence:

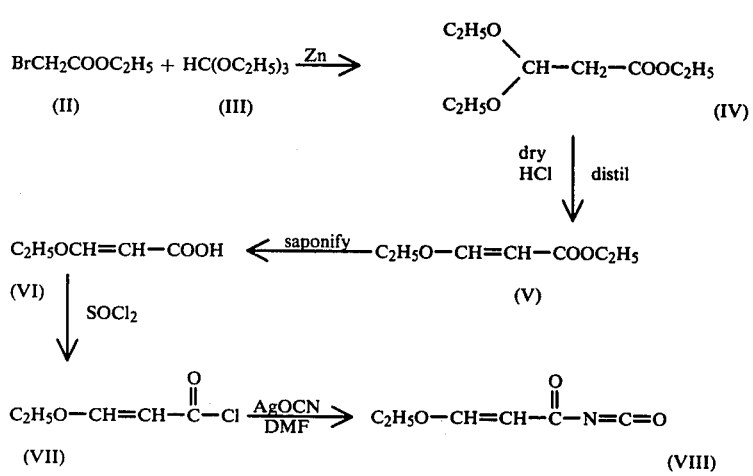

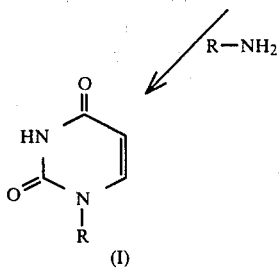

wherein R is as previously defined.

Generally, the above reaction involves adding in dropwise manner a solution of Compounds II and III in benzene to benzene containing dried zinc, refluxing the mixture, separating Compound IV from the mixture, and distilling Compound IV in the presence of triethylamine hydrochloride and butylated hydroxytoluene until no more volatiles passed over. Compound V is separated from the mixture and added to a solution of NaOH dissolved in $H_2O$ which is then heated until the solution turns orange-red. This solution is acidified to form Compound VI in the form of yellow crystals which are then separated from the solution and added to a solution of NaOH pellets dissolved in 400 ml. of methyl alcohol to form an orange precipitate of the sodium salt

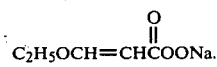

The salt is reacted with $SOCl_2$ to form the corresponding acid chloride (Compound VII) to which is added AgOCN to form Compound VIII which is then separated from the mixture. Compound VIII is reacted with an aniline after which the reaction product is reacted with NaOH and ethanol to form Compound I wherein R is as aforesaid.

DETAILED DESCRIPTION OF THE INVENTION

The compounds of this invention may be orally administered to poultry in a suitable carrier therefor. It is generally convenient and, therefore, preferred to add the agents to the poultry feed so that a therapeutic dosage of the agent is ingested with the daily poultry ration. The agent may be added directly to the feed, as such, or in the form of a premix or concentrate. A premix or concentrate of therapeutic agent in a carrier is commonly employed for the inclusion of the agent in the feed. Suitable carriers are liquid or solid, as desired, such as water, various meals; for example, soybean oil meal, linseed oil meal, corncob meal, and mineral mixes such as are commonly employed in poultry feeds. A particularly effective carrier is the poultry feed itself; that is, a small portion of poultry feed. The carrier facilitates uniform distribution of the active materials in the finished feed with which the premix is blended. This is important because only small proportions of the present potent agents are required. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. it will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to poultry. In such instances, the poultry is permitted to consume the usual diet. Alternatively, such concentrated supplements may be added directly to the poultry feed to produce a nutritionally balanced, finished feed containing a therapeutically effective level of one or more of the compounds of this invention. The mixtures are thoroughly blended by standard procedures, such as in a twin shell blender, to ensure homogeneity. The finished poultry feed should contain roughly between 50% and 80% of grains, between 0% and 10% animal protein, between 5% and 30% vegetable protein, between 2% and 4% minerals, together with supplemental vitaminaceous sources.

It will, of course, be obvious to those skilled in the art that the use levels of the compounds described herein will vary under different cicumstances. Continuous low-level medication, during the growing period; that is, during the first 8 to 12 weeks for chickens, is an effective prophylatic measure. In the treatment of established infections, higher levels may be necessary to overcome the infection.

The present compounds may be employed at substantially low levels in feeds for the prevention or treatment of coccidiosis. Generally, the feed compositions of the present invention comprise a minor amount of the compounds of this invention and a major amount of a nutritionally balanced feed. Feed compositions containing 0.0060%–0.0500% by weight in the feed of the present agent are found to effectively combat coccidiosis. When administered by incorporation into the drinking water, preferably as an alkali metal or alkaline earth salt, the herein described compounds are used at levels one-half the dosage given above for feeds.

The present feed compositions and supplements may also contain other effective therapeutic agents such as antibiotics to promote growth and general health of the poultry as well as sulfa compounds which may increase the effectiveness of the present coccidiostats.

The cocciodiostatic activity of the compounds of the present invention is demonstrated as follows Groups of five nine-day old Barred Rock Cross strain cockerels are fed a basal ration into which the test compound is incorporated at various concentrations. The basal ration, a commercial chick starter (Purina Commercial Chick Starter, available from the Ralston Purina Co., St. Louis, Mo.), having the following composition, is presented ad libitum to the chicks 24 hours before infection and continuously thereafter throughout the course of the tests.

Basal Ration Composition

| Crude protein not less than | 18.0% |
|---|---|
| Crude fat not less than | 3.0 |
| Crude fiber not more than | 6.0 |
| Added minerals not more than | 3.5 | supplied by the following ingredients:

Meat and bone meal, fish meal, soybean meal, ground barley, ground oats, ground yellow corn, dehydrated alfalfa meal, wheat middlings, vitamin $B_{12}$ supplement, ethoxyquin (a preservative), animal fat preserved with BHA*, chlorine chloride, niacin, vitamin A supplement, roboflavin supplement, calcium pantothenate, D activated animal sterol, vitamin E supplement, menadione sodium bisulfite (source of vitamin K activity)**, calcium carbonate, low fluorine rock phosphate, iodized salt, manganese sulfate, manganous oxide, copper sulfate, zinc oxide

*BHA=butylated hydroxyanisole
**menadione sodium bisulfite=2-methyl-1,4-naphthaquinone sodium bisulfite Twenty-four hours after initiation of the medication the chicks are inoculated orally with 200,000 sporulated oocysts (*Eimeria tenella*) and the average weight per bird per group determined. In addition, a group of ten chicks is fed the basal ration which contains none of the test compound (infected, untreated controls). A further group of ten chicks serves as uninfected, untreated controls. The chicks are examined on the fifth and sixth day post-infection for signs of hemorrhage. On the eighth day post-infection, the average body weight per bird per group is determined, the birds necropsied, the cecum examined macroscopically, and a pathology index (average degree of infection [A.D.I.]) determined. Chicks which die prior to the fifth day post-infection are considered as toxic deaths. Those which die five days post-infection or later are considered as deaths due to disease. The efficacy of the test compound is judged by the prevention of mortality and by comparison of the pathologic index with that of the unmedicated infected controls. The degree of pathologic involvement at necropsy is expressed as the average degree based on the following scheme: 0=no cecal lesions; 1=slight lesions; 2=moderate lesions; 3=severe lesions; 4=death.

The concentration of test compound in the feed which will produce normal weight gains relative to the uninfected, untreated controls and normal pathology relative to the infected, untreated controls, referred to as the minimum effective concentration (MEC), is thus found to be 0.006%.

In like manner, the coccidiostatic activity of the compounds of the Examples is determined.

Various levels of the compounds of the invention are thoroughly blended into a nutritionally balanced diet having the composition shown below.

| | Percent |
|---|---|
| Ground yellow corn | 51.28 |
| Soybean oil meal (51%) | 38.15 |
| Corn oil | 6.10 |
| $CaCO_3$ | 1.20 |

| | Percent |
|---|---|
| Dicalcium phosphate | 1.35 |
| Salt | 0.61 |
| Delamix (commercially available mineral mix containing $CaCO_3$ and small amounts of iron, zinc, manganese, and so forth salts. Limestone Products Corporation of America, New Jersey | 0.1 |
| Vitamin A (5305 I.U./lb.) | 0.1 |
| Vitamin $D_3$ (681 I.C.U./lb.) | 0.05 |
| Klotogen F (Commercially available form of vitamin K, Abbott Laboratories) | 0.0003 |
| Pyridoxine hydrochloride | 0.0006 |
| D.I.-methionine | 0.140 |
| Niacin U.S.P. | 0.0025 |
| Choline chloride (25%) | 0.2 |
| Riboflavin | 0.06 |
| Calcium pentothenate (45%) | 0.002 |
| Myvanix (commercially available form of vitamin E) | 0.005 |

Such feeds, when administered ad libitum to nine-day old chicks and to medium-sized turkey poults infected with *E. tenella* as described above are effective in controlling the coccidial infection.

The MIC values (minimum inhibitory concentration) of the compounds of the examples are as follows:

MIC (% by wt. in feed)

Example 1—0.0230
Example 2—0.0500
Example 3—0.0060
Example 4— <0.0125
Example 5—0.0500
Example 6—0.0125

The following examples illustrate the invention

EXAMPLE 1

1,(3,5-Dimethylphenyl)-2,4-(1H, 3H) pyrimidinedione 500 grams of zinc (mossy) were slurried in 1 L 2 N HCL for 5 min. after which it was filtered and washed 3 times each in 1 L of $H_2O$, 1 L of MeOH and 1 L of acetone. The zinc was dried in a vacuum over at 100° for 10 minutes and then placed in a 2 L RB flask equipped with a stirrer, condenser and funnel under $N_2$. To this 300 ml of benzene and a few iodine crystals were added and heated to reflux. Added in dropwise manner over about 2½ hrs. was a solution of 125 grams of ethylbromoacetate and 135 grams of ethylorthoformate in 400 ml of benzene. The mixture was refluxed further for 10 hours. The resulting amber liquid was then poured into a mixture of 800 ml ether and 400 ml $H_2O$. Some HOAC was added to get 2 clear phases. The ether was separated and the remainder washed 3 times in $H_2O$, 4 times in $NaHCO_3$ and 3 times in $H_2O$ after which it was dried over $Na_2SO_4$ and evaporated to yield a dark oil.

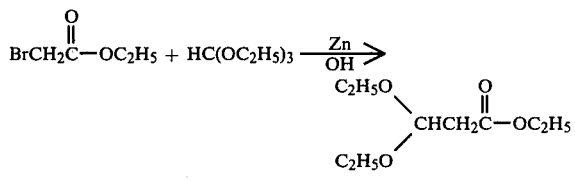

101.7 grams of the reaction product were placed in a distillation assembly under N₂ at atmospheric pressure and heated to bath temperature of 225°–230° C. for 6 hrs. It was cooled to room temperature and allowed to stand overnight. A small amount of BHT was added to the solution along with a capillary (ebullition tube) through which N₂ was introduced into the solution. The solution was then distilled under reduced pressure to yield two fractions taken at 82°–85° C./10 min. and 85°–86° C./10 min. The two fractions were combined (94 grams) and replaced in the reaction setup described above except that metroware flasks, etc. were used. The fractions were heated in the presence of a catalytic amount of triethylamine-HCL and 1.0 gram of BHT to bath temperature of 225°–230° C. until no more volatiles came over (about 2 hrs.) after which the solution was cooled. 21 ml (17 grams) of ethanol were collected along with 62 grams of clear oil after distillation.

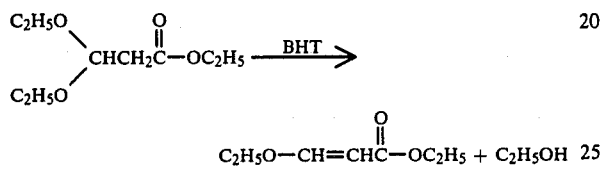

62 grams of the clear oil collected were then added to a solution of 20 grams of NaOH dissolved in 650 ml of H₂O under N₂. The mixture was slowly heated to internal temperature of 80°–90° C. to produce a solution which started to turn orange-red after about ½ hr. The solution was cooled in an ice bath and made acidic with 6NHCL after which yellow crystals were filtered and washed with H₂O. The crystals were dried in an oven overnight to yield 31.6 grams, mp 104°–105° C.

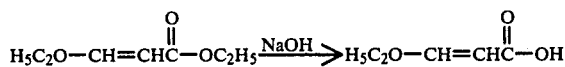

8.8 grams of sodium hydroxide pellets were dissolved in 400 ml of methyl alcohol. The solution was cooled in an ice bath and 24.2 grams of

were added portionwise. An orange precipitate formed which was stirred at room temperature for 1 hour and dried in an oven. The yield of the sodium salt was 27.6 grams

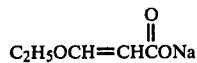 (a)

10 grams of (a) were reacted with 20 ml of neat thionyl chloride at room temperature for 3½ hrs. after which an equal volume of ether (200 ml) was added to precipitate the acid chloride formed.

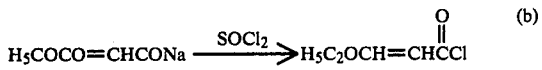 (b)

The reaction product was stirred overnight and then filtered under a nitrogen blanket and rinsed in fresh ether (20 ml). The ether was then evaporated from the product and the ether replaced with benzene several times to remove excess SOCl₂. The acid chloride oil weighed 4.8 grams.

The acid chloride was dissolved in fresh benzene and placed in a flask equipped with a mag. stirrer, thermometer and concenser under nitrogen. The mixture was cooled to 10° C. and 10.7 grams of AgOCN were added in three portions. The mixture was cooled to room temperature and then heated to 45° for five minutes. The mixture cooled by itself in the water bath and was stirred for 3 hrs. after which the silver salts were filtered off.

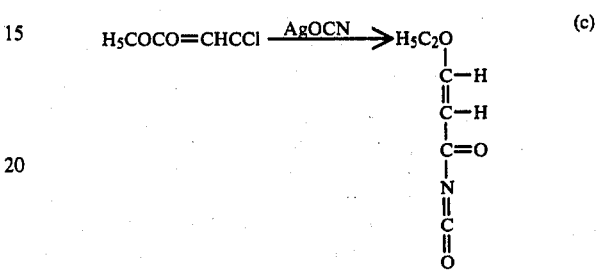 (c)

The filtrate was placed in an ice cold, stirred solution of 8.8 grams of 3,5-dimethylaniline in 250 ml of diethylene oxide under N₂. A precipitate formed which was stirred for 2 hours and filtered to yield 8.2 grams with a melting point of 182°–185° C. The product was dissolved in hot 3-A ethanol and recrystallized to yield 3.4 grams with a melting point of 200°–202° C. The mother liquor (M/L) was rotovaced to a dry state and triturated in diethyl ether, filtered and air dried to yield 1.2 grams having a melting point of 122°–25° C.

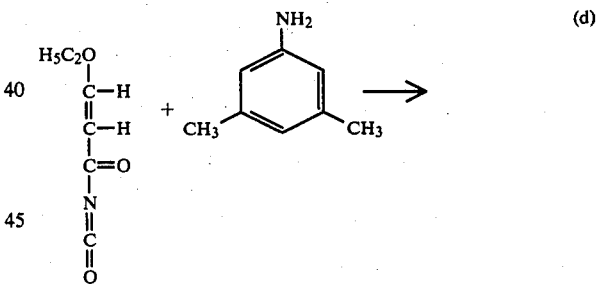 (d)

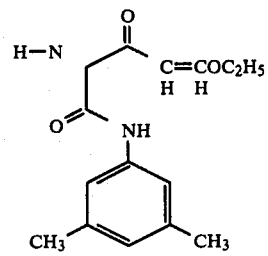

4.4 grams of (d), 100 ml of ethanol and 100 ml of 2 N NaOH were placed in a 500 ml RBF with condenser, mag. stirrer and steam bath and brought to reflux for about 1 hr. and then cooled to room temperature. 100 ml of CHCL₃ were extracted three times, the resulting material dried over Na₂SO₄ and the solvent drawn off on a Buchi to yield a yellow, sticky cake. The cake was slurried in 10% HCL, filtered and air dried over night. This was taken up in 10° Na₂SO₄ then brought back out with 1 N HCl and refiltered to yield 2.6 grams, mp 89°-96° C. The reaction product was recrystallized from a mixture of chloroform and methyl alcohol to yield gum and oil. The M/L was rotovaced down to a salt, extracted with CHCl₃ and rotovaced down to a salt, extracted with CHCl₃ and rotovaced down to a sticky solid, weighing 0.52 grams. Upon contact with air the material turned from a flaky solid to a gummy consistency. The gum and CHCl₃ was concentrated to dryness and triturate in tetrahydrofuran. The filtered solid weighed 0.49 grams, mp 163°-65° C. It was recrystallized to yield 0.42 grams mp 173°-174° C. of 1-(3,5-dimethylphenyl)-2,4,(1H,3H) pyrimidinedione.

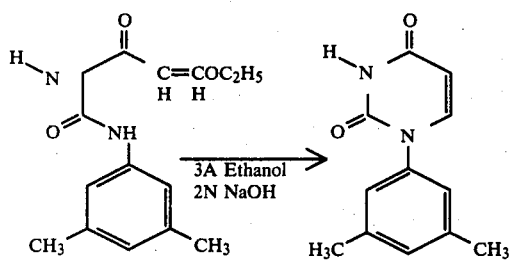

(e)

EXAMPLE 2

1-[3-chloro-4-(p-chlorophenoxy)phenyl]-2,4(1H,3H)-pyrimidinedione

The steps of Example 1 were repeated with the differences that in (b), 5 grams of the sodium salt and 200 ml of thionyl chloride were used while in (c) 5.3 grams of AgOCN was used. In (d), 9.1 grams of p-chlorophenoxy-3-chloroaniline replaced the aniline used. In (e), 5.1 grams of the reaction product of (d) was used instead of 4.4 grams.

As for the reaction product of (c), 5.1 grams were produced with a melting point of 225°-226° C. In reaction (d) the ingredients were refluxed for 2 hrs. and the product was acidified to about 3 with 1 N HCL. 4.5 grams of the product were produced with a mp of 258°-259° C. After slurrying the product in 1 N HCl, filtering and oven drying the product a yield of 3.9 grams mp 254°-256° C. of 1-[3-chloro-4(p-chlorophenoxy)phenyl]-2,4(1H,3H)-pyrimidineodione was achieved.

The formula for the final product was

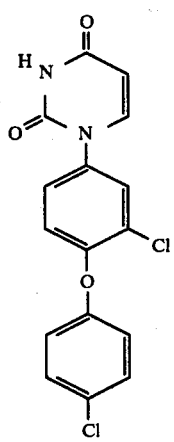

EXAMPLE 3

1-[5-chloro-4-(p-chlorophenylthio)-3-methylphenyl]-2,4-(1H,3H)pyrimidinedione.

6 grams of the reaction product (a) of Example 1 was added portionwise to 20 ml of ice cold SOCl₂ in an RB flask while stirring and excluding air. The mixture cooled to room temperature and stirred for 1 hr. an equal volume of diethylene oxide was added and stirred overnight at room temperature. The precipitated salt was then filtered under a N₂ blanket after which the ether was retovaced off and replaced three times with benzene to get rid of SOCl₂. The product was dissolved in 100 ml of fresh benzene and placed in an RB flask under N₂ with a condenser, thermometer and stopper. The mixture was cooled to 10° C. and 6.5 grams of AgOCN was added in one portion. The temperature of the mixture was raised to room temperature then warmed in a water bath to 45°-50° C. The mixture was then allowed to come to room temperature over 3 hrs. The silver salts were filtered off and benzene was added to an ice cold solution of 12.3 grams of 3,5-dimethylaniline in diethylene oxide (300 ml). A precipitate formed which was stirred at room temperature overnight. It was filtered to yield 40 g mp 224°-226° C. The filtrate was evaporated and titrated in hexane to yield 10.4 g, mp 130°-133° C. The resulting compound was

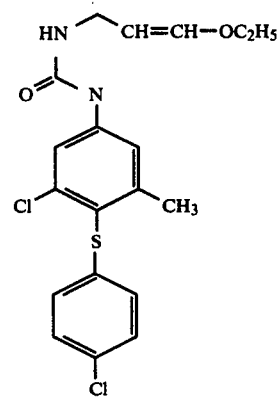

4.0 grams of the above were mixed with 75 ml of 2 N N₂OH and 75 ml of 3 A ethanol in a RBF with reflux condenser, steam bath and magnetic stirrer. They were refluxed for 1 hr., cooled to room temperature and acidified with concentrated HCL to about 2. A precipitate formed which was filtered to yield 2.5 grams, mp 220°-225° C. The material was slurried in HCL for ½ hr. to yield 2.3 grams, mp 220°-227° C. of 1-[5-chloro-4-(p-chlorophenylthio)-3-methylphenyl]-2,4-(1H,3H) pyrimidinedione. The M/L after standing yielded a second crop of dark brown crystals weighing 0.50 grams, mp 150°-160° C.

The formula for the compound was:

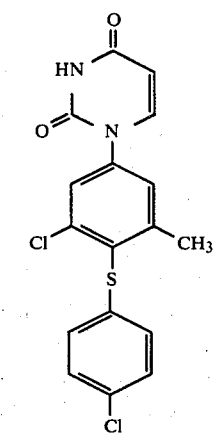

EXAMPLE 4

1-[5-chloro-4-(p-chlorophenylsulfonyl)-3-methyl-phenyl]-2,4-(1H,3H)pyrimidinedione The product of Example 3 (1.23 grams) was combined with 2 ml of $H_2O_2$ and 20 ml of HOAC and stirred at room temperature. The mixture was warmed in a steam bath for 1½ hrs. and was stirred at room temperature over a weekend. $H_2O$ was poured on the precipitate formed after which the mixture was filtrated and air dried to yield 1.5 grams. When added to $CHCl_3$/meoH (1:1), and recrystalized directly therefrom the yield was 0.38 grams, mp 247°–48° C. A second crop yielded 0.08 grams, mp 246°–48° C. while a still further crop yielded 0.099 grams, mp 235°–242° C. The formula for the final product was:

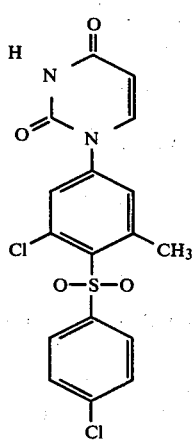

EXAMPLE 5

1-[3,5-dimethyl-4-(p-chlorophenylthio)phenyl]2,4-(1H,3H)-pyrimidinedione 20.7 grams of

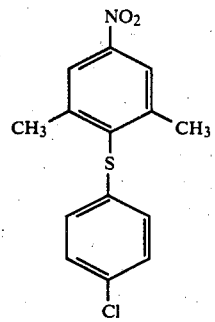

and 150 ml of 3A ethanol in slurry were added to a 3-necked, 1 liter round bottom flask equipped with a magnetic stirrer, condenser thermometer and a funnel. To this, was added in dropwise fashion a solution of 62 grams of $SnCl_2.2H_2O$ in HCl. The mixture was then heated to reflux on a steam bath for 4 hrs. after which it was cooled and poured on 1.5 $1H_2O$/ice, filtered and dried to yield 18.5 grams of the HCl salt of the amine which was then stirred in 600 ml. of saturated $NaHCO_3$ solution for about 1 hr. to get rid of HCl salt and liberate the free base. This resulting aniline was filtered and dried to yield 16.0 grams of product, mp 156° C. The formula for the product is:

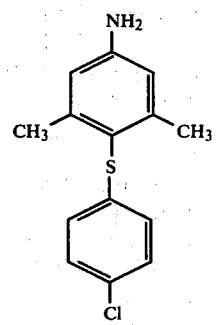

8.9 grams of the above product were combined with the product of (c) in Example 1 prepared as set forth in that Example but using the following amounts of components:

| | | |
|---|---|---|
| (a) | 5.0 | grams |
| thionylchloride | 10.0 | ml |
| ether | 100 | ml |
| AgNCO | 5.2 | grams |

The mixture of the isocyanate with the aniline was stirred at room temperature overnight, filtered and air dried to yield 3.6 grams, mp 231° C. The M/L was evaporated and the residue was triturated in diethylene oxide after which it was filtered to yield 0.9 grams, mp 117°–130° C. which was primarily aniline. 2.0 grams, mp 236°–237° C. more of the primary compound were received from $CHCl_3$/MeOH (1:1). A second crop yielded 0.4 grams mp 236°–237° C. The formula for the recovered product was:

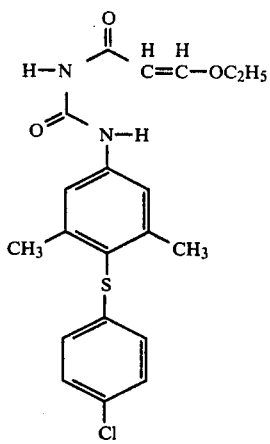

2.4 grams of this recovered product were combined with 50 ml of 2 N NaOH and a like amount of 3 A ethanol in a RB flask equipped with a mag. stirrer and reflux condenser. The flask was heated with a steam bath. The ingredients were heated to reflux for 1 hr., allowed to cool to room temperature, acidified with 1 N HCL and then filtered. The solid was then recrystallized to 1.07 grams, mp 212°–213° C. The formula for the product was:

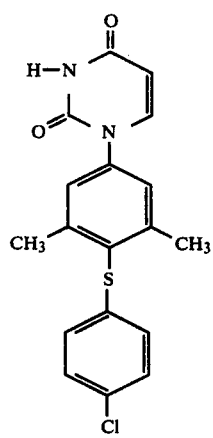

EXAMPLE 6

1-(3,5-dichlorophenyl)-2,4-(1H,3H) pyrimidinedione

This compound was prepared in the same manner as the compound of Example 1 except that 3,5-dichloroaniline was used in step (d) instead of 3,5-dimethylaniline.

What is claimed is:

1. A compound of the formula

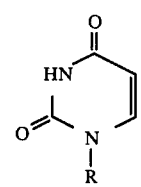

wherein R is

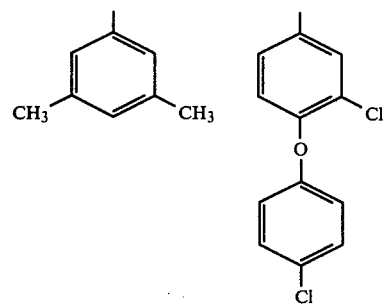

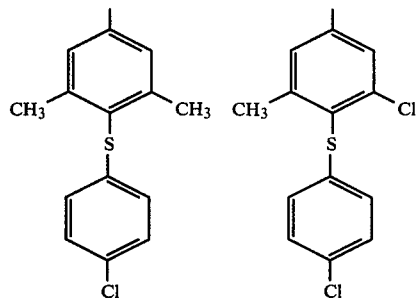

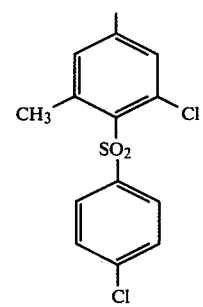

2. A compound selected from the group consisting of 1-[3-chloro-4-(p-chlorophenoxy)phenyl]uracil, 1-[5-chloro-4-(p-chlorophenylsulfonyl)-3-methylphenyl]uracil and 1-[3,5-dimethyl-4-(p-chlorophenylthio)phenyl] uracil.

* * * * *